United States Patent [19]

Matharu et al.

[11] 4,010,268
[45] Mar. 1, 1977

[54] DERIVATIVES OF HEXAHYDRODIBENZOFURAN-3-ONE, THEIR PREPARATION AND USE IN PHARMACEUTICAL COMPOSITIONS

[75] Inventors: Saroop Singh Matharu, Highworth; David Alun Rowlands, Cirencester; Robert Westwood, Cricklade; John Bodenham Taylor, Down Ampley, all of England

[73] Assignee: Roussel-UCLAF, Paris, France

[22] Filed: Apr. 24, 1975

[21] Appl. No.: 571,236

[30] Foreign Application Priority Data

Apr. 26, 1974 United Kingdom ............ 18459/74

[52] U.S. Cl. .......................... 424/250; 424/248.54; 424/267; 424/274; 424/285; 260/247.2 A; 260/268 TR; 260/293.58; 260/326.34; 260/346.2 M

[51] Int. Cl.$^2$ ..................................... C07D 405/12
[58] Field of Search ................ 260/326.34, 293.58, 260/247.2 A, 268 TR, 346.2 M; 424/250, 248, 274, 267, 285

[56] References Cited

UNITED STATES PATENTS 3,646,060  2/1972  Morlock et al. ........... 260/346.2 M

Primary Examiner—Donald G. Daus
Assistant Examiner—Jose Tovar
Attorney, Agent, or Firm—Bacon & Thomas

[57] ABSTRACT

The present invention relates to derivatives of hexahydrodibenzofuran-3-one and their salts possessing interesting antitussive activity, their process of preparation, intermediates, and pharmaceutical compositions.

9 Claims, No Drawings

DERIVATIVES OF HEXAHYDRODIBENZOFURAN-3-ONE, THEIR PREPARATION AND USE IN PHARMACEUTICAL COMPOSITIONS

The present invention relates to derivatives of hexahydrodibenzofuran-3-one and their salts possessing interesting antitussive activity.

According to the present invention there are provided compounds of the general formula

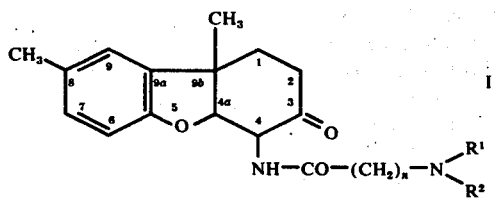

where $R^1$ and $R^2$ which may be the same or different represent hydrogen atoms, or lower alkyl groups which may be unsubstituted or which may carry amino or aryl substituents, or together with the intervening N represent a saturated heterocyclic group which may include one or more further hetero atoms and which may be unsubstituted or which may carry alkyl, hydroxyalkyl, aryl, aralkyl, acyl or alkoxycarbonyl substituents; and $n$ represents an integer less than 6; and their salts with acids.

Typically, the lower alkyl groups may have 1 to 6 carbon atoms, e.g. especially the methyl, ethyl, propyl, isopropyl and butyl groups. The aryl groups may, in particular, be carbocyclic aryl groups such as phenyl groups, benzyl and phenethyl groups. Possible amino substituents include primary amine groups as well as N-alkyl- and N,N-dialkyl-amino groups.

The saturated heterocyclic group may, for example, have 5–7 ring atoms. Other heteroatoms present apart from the linking nitrogen atom may, for example, be further nitrogen atoms as in the piperazine ring or oxygen atoms as in the morpholine ring.

Acyl groups include particularly carboxylic acyl groups such as lower alkanoyl groups e.g. acetyl, propionyl or butyryl groups.

Especially noteworthy compounds are those in which the identical or different groups $R^1$ and $R^2$ represent methyl, ethyl, benzyl or dimethylaminoethyl groups or together with the intervening N represent a pyrrolidino, piperidino, morpholino or piperazino (piperazin-1-yl) group or a piperazin-1-yl group substituted at the 4-position by a methyl, ethyl, hydroxyethyl, phenyl, benzyl, acetyl or ethoxycarbonyl group; and preferably those compounds in which $R^1$ and $R^2$ represent methyl groups or together with the intervening N represent a 4-methylpiperazin-1-yl group.

It will be seen that the formula I is capable of configuration isomerism in the 4, 4a and 9b positions. In particular the 4α-substituted compounds in the 4aβ, 9bβ, series may be mentioned as possessing valuable activity.

As especially preferred compounds may be mentioned: 8,9bβ-dimethyl-1,2,3,4,4aβ,9b-hexahydro-4-α[3-(4-methyl-piperazin-1-yl)-propionamido]-dibenzofuran-3-one; 8,9bβ-dimethyl-1,2,3,4,4aβ,9b-hexahydro-4α-[3-N,N-dimethylamino-propionamido]-dibenzofuran-3-one; 8,9bβ-1,2,3,4,4aβ,9b-hexahydro-4α-[3-piperazinopropionamido]-dibenzofuran-3-one; 8,9bβ-dimethyl-1,2,3,4,4aβ,9b-hexahydro-4α-[4-(4-methylpiperazin-1-yl)-butyramido]-dibenzofuran-3-one; and 8,9bβ-dimethyl-1,2,3,4,4aβ,9b-hexahydro-4α-[5-N,N-dimethylamino-valeramido]-dibenzofuran-3-one; and their salts.

Acid addition salts may be formed, for example, with mineral or organic acids, e.g. hydrochloric, hydrobromo, nitric, sulphuric, phosphoric, acetic, formic, benzoic, maleic, fumaric, succinic, tartaric, citric, oxalic, benzilic, glyoxylic or aspartic acid or an alkanesulphonic or aryl sulphonic acid such as methanesulphonic or p-toluenesulphonic acid.

According to a further feature of the present invention there is provided a process for the preparation of compounds of the general formula I and their salts in which 8,9b-dimethyl-1,2,3,4,4a,9b-hexahydro-4-aminodibenzofuran-3-one (V) is reacted with an acyl halide of general formula

where $Hal^1$ and $Hal^2$ (which may be the same or different) represent halogen atoms and $n$ is as defined above, to give an intermediate of the general formula

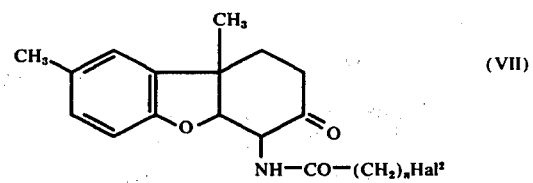

(where $n$ and $Hal^2$ are as defined above) which is reacted with a compound of the general formula

(where $R^1$ and $R^2$ are as defined above) to yield a compound of the general formula I and, if desired, reaction with an acid to form a salt thereof. Since the process does not affect the stereochemistry at the 4-position, selecting the appropriate starting isomer gives the same isomer I and thus 8,9bβ-dimethyl-1,2,3,4,4aβ,9bβ-hexahydro-4α-aminodibenzofuran-3-one gives the appropriate 4aβ,9bβ, 4α product.

The reaction of the starting material V with the halide of formula VI is preferably effected in a solvent, such as benzene or benzene/chloroform mixture, and in the presence of a base capable of neutralising the acid $Hal^1$ H formed, e.g. an alkali metal carbonate or a tertiary nitrogen base, such as sodium carbonate or pyridine. $Hal^1$ and $Hal^2$ preferably represent chlorine atoms.

The reaction with the compound of formula VIII is also preferably effected in a solvent such as benzene or toluene. Both reactions are preferably effected at a moderately elevated temperature, e.g. the reflux temperature of the system.

Starting material of formula V may be prepared by either of the following reaction sequences:

a. The compound of formula (II) is reacted with a salt of hydroxylamine to form the corresponding oxime (III) which is reacted with an arylsulphonyl halide to give the O-arylsulphonyloxime (IV) which is reacted with an alkali metal alkoxide, e.g. sodium ethoxide, to give the 4α-amino starting material V as shown in the following reaction scheme:

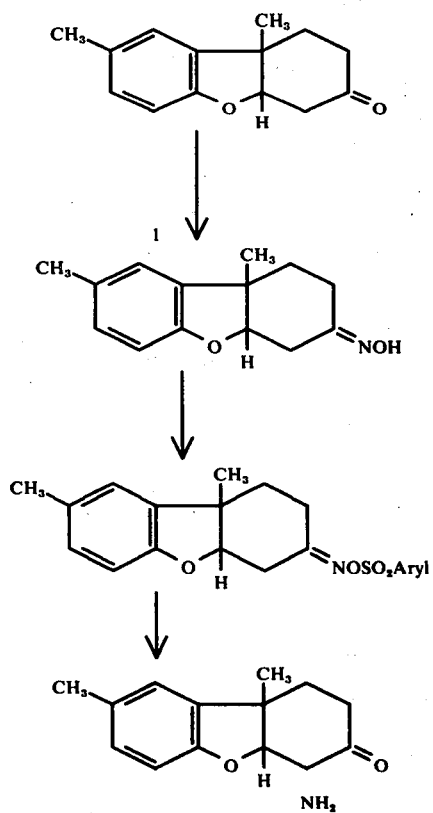

The reaction with hydroxylamine is preferably effected in the presence of an alkali metal acetate e.g. sodium acetate. The reaction with the sulphonyl halide is preferably effected under anhydrous conditions in a solvent such as pyridine, using a sulphonyl chloride such as p-toluenesulphonyl chloride. The reaction with the alkoxide is preferably effected at a reduced temperature, e.g. in an ice bath.

or b. The compound of formula (II) is reacted with an alkyl nitrite containing 4 to 6 carbon atoms to yield a compound of formula (IX)

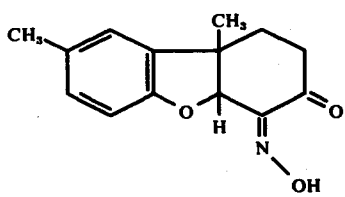

which is subsequently reduced by hydrogen in the presence of a catalyst to form a product of formula (VA) in admixture with its 4β-amino isomer. The reaction with the alkyl nitrite is preferably effected under acid conditions, for example in the presence of hydrochloric acid. The catalyst used in the hydrogenation may, for example, be a noble metal catalyst such as palladium on charcoal.

The compounds according to the present invention, especially the 4aβ, 9bβ, 4α isomers, exhibit useful activity in controlling various forms of cough including those originating in the bronchopulmonary tract, reflex, spasmodic or irritating coughs and whooping cough (pertussis) and in the treatment of bronchitis and asthma.

The dose will vary with the particular ailment being treated, the subject, the compound and the route of administration. A typical range would be from 1–125 mg, e.g. 25–100 mg, per day in an adult when administered orally.

According to a further feature of the present invention there are provided pharmaceutical compositions comprising one or more compounds of the general formula I or salts thereof as active ingredient together with a pharmaceutical carrier or excipient. The compositions will normally be in a form suitable for oral administration, such as tablets, coated tablets, capsules, granules, solutions, syrups and linctuses. Occasional need may arise for other routes of administration in which case the compositions may be formulated as, for example, suppositories, injectable preparations or aerosols.

The compositions are conveniently formulated in dosage units such as tablets, capsules, suppositories and metered-dose sprays. Each dosage unit would typically contain 5–50 mg, e.g. 10–25 mg. of the compound according to the invention.

Conventional carrier and excipient ingredients may be used, such as talc, gum arabic, lactose, starch, magnesium stearate, cocoa butter, animal and vegetable fats, paraffin derivatives, glycols and various wetting, dispersing, emulsifying, flavouring, colouring and preserving agents.

The starting materials of formula VII are also of particular interest as novel compounds, especially:
8,9bβ-dimethyl-1,2,3,4,4aβ,9b-hexahydro-4α-(2-chloroacetamido)-dibenzofuran-3-one;
8,9bβ-dimethyl-1,2,3,4,4aβ,9b-hexahydro-4α-(3-chloropropionamido)-dibenzofuran-3-one;
8,9bβ-dimethyl-1,2,3,4,4aβ,9b-hexahydro-4α-(4-chlorobutyramido)-dibenzofuran-3-one;
8,9bβ-dimethyl-1,2,3,4,4aβ,9b-hexahydro-4α-(5-chlorovaleramido)-dibenzofuran-3-one; and
8,9bβ-dimethyl-1,2,3,4,4aβ,9b-hexahydro-4α-(6-bromohexanamido)-dibenzofuran-3-one.

The following Preparations and Examples further illustrate the invention, but should not be construed as limiting the invention.

PREPARATION
1—4α-AMINO-8,9bβ-DIMETHYL-1,2,3,4,4aβ,9b-HEXAHYDRODIBENZOFURAN-3-ONE HYDROCHLORIDE

Step
A—8,9bβ-dimethyl-1,2,3,4,4aβ,9b-hexahydrodibenzofuran-3-one oxime 8,9bβ-dimethyl-1,2,3,4,4aβ,9b-hexahydrodibenzofuran-3-one (150g, 0.69 mole) was dissolved in hot ethanol (375 mls) and hydroxylamine hydrochloride solution (60g, 0.855 mole in water 225 mls) and sodium acetate (75g, 0.915 mole) were added with swirling. The solution was heated on a water bath until the oxime started to crystallize. T.L.C. at this stage indicated that no starting material was left. Water (100 mls) was then added and the flask was left to cool in an ice bath. After filtering and washing well with water (0.5 liters), the 8,9bβ-dimethyl-1,2,3,4,4aβ,9b-hexahydrodibenzofuran-3-one oxime thus obtained was dried under vacuum over $P_2O_5$ to constant weight. Yield 158g, 99%. Colourless crystals, M. pt. 160° – 162° C.

Step B—8,9bβ-dimethyl-1,2,3,4,4aβ,9b-hexahydrodibenzofuran-3-one oxime tosylate

Tosyl chloride (160g, 0.84 mole) was dissolved in dry pyridine (300 mls) and the solution was stirred and cooled to 0° C in an ice/salt bath. A solution of the 8,9bβ-dimethyl-1,2,3,4,4aβ,9b-hexahydrodibenzofuran-3-one oxime (97g, 0.42 moles) in dry pyridine was then added at such a rate that the temperature remained below 10° C. After 2 hours, T.L.C. indicated that no starting material remained and so the reaction mixture was poured onto iced water (4 liters) causing the oxime tosylate to precipitate out. The product was filtered off, washed well with water (1+ liters) and then with cold methanol (0.5 liter) and dried to constant weight under vacuum over $P_2O_5$. Yield 158g, 98% M. pt. 130° – 132° C.

Step C—4α-amino-8,9bβ-dimethyl-1,2,3,4,4aβ,9b-hexahydrodibenzofuran-3-one hydrochloride Sodium metal (14.7g, 0.63 mole) was dissolved in dry ethanol (1 liter) and then cooled in an ice bath. The 8,9bβ-dimethyl-1,2,3,4,4aβ,9b-hexahydrodibenzofuran-3-one oxime tosylate (230g, 0.61 mole) was added with vigorous mechanical stirring. After stirring for 4 hours at ice bath temperature, the mixture was stirred overnight at room temperature. The mixture was then filtered and the residue was washed with dry ether (2 × 200 mls). The filtrate was concentrated to about 250 mls and was then poured into cold 10% hydrochloric acid (500 mls) in a separating funnel along with ether (500 mls). The acidic aqueous layer was removed and the ether layer further extracted with 10% hydrochloric acid (2 × 125 mls). The combined acid extracts were washed once with ether (200 mls) and then reduced in volume at 50° C on a rotary evaporator until crystallization commenced. The mixture was then cooled and filtered, the filtrate being further reduced in volume to obtain second and third crops. The 4α-amino-8,9bβ-dimethyl-1,2,3,4,4aβ,9b-hexahydrodibenzofuran-3-one hydrochloride thus obtained was washed with a little acetone and dried under vacuum over $P_2O_5$. Yield 136 g, 85%. Colourless needles, M. pt. 187° – 191° C.

PREPARATION 2

4-amino-8,9bβ-dimethyl-1,2,3,4,4aβ,9b-hexahydrodibenzofuran-3-one hydrochloride

Step A—8,9bβ-dimethyl-1,2,3,4,4aβ,9b-hexahydro-4-oximinodibenzofuran-3-one.

8,9bβ-dimethyl-1,2,3,4,4aβ,9b-hexahydrodibenzofuran-3-one (5g) was dissolved in ethyl acetate and isoamyl nitrite (1.4 molar equivalents) and concentrated hydrochloric acid (1 ml.) were added. The mixture stood at room temperature for 4 hours. Then water was added and the organic layer removed. Chromatography on silica using ethyl acetate/petroleum ether as eluent gave the required oximino ketone (1.5g) M. pt. 231°–232° C.

IR. spectrum peaks 750, 972, 984, 1499, 1718, 3295 cm

Step B: 4-amino-8,9bβ-dimethyl-1,2,3,4,4aβ,9b-hexahydrodibenzofuran-3-one-hydrochloride.

8,9bβ-dimethyl-1,2,3,4,4aβ,9b-hexahydro-4-oximino dibenzofuran-3-one (1.0g) was dissolved in ethanol and 5% Pd/C catalyst (500 mg.) and conc. hydrochloric acid (1 ml) were added. Hydrogenation was complete in 2 hours. Filtering and removal of solvent gave a solid hydrochloride salt of 4-amino-8,9bβ-dimethyl-1,2,3,4,4aβ,9b-hexahydrodibenzofuran-3-one.

EXAMPLE 1

8,9bβ-Dimethyl-1,2,3,4,4aβ,9b-hexahydro-4α-[3-(4-methylpiperazin-1-yl)propionamido] dibenzofuran-3-one hydrochloride Step A—8,9bβ-dimethyl-1,2,3,4,4aβ,9b-hexahydro-4α-(3-chloro propionamido) dibenzofuran-3-one 4α-Amino-8,9bβ-dimethyl-1,2,3,4,4aβ,9b-hexahydrodibenzofuran-3-one hydrochloride (53.5g, 0.20 mole) was suspended in benzene-chloroform (1 : 1, 1 liter) and 3-chloropropionyl chloride (50.8g; 0.40 mole) was added with anhydrous sodium carbonate (100g, 0.94 mole). The mixture was stirred at 60° – 65° C for 4 to 6 hours, after which time T.L.C. evidence showed that the reaction was completed. The reaction mixture was poured into water (1 liter), the organic layer was separated and the aqueous layer was further extracted with chloroform (2 × 200 mls). The combined organic layers were then washed thoroughly with water and were dried over magnesium sulphate. After removal of drying agent and solvent, the oil obtained was triturated with ether to give the 8,9bβ-dimethyl-1,2,3,4,4aβ,9b-hexahydro-4α-(3-chloropropionamido)-dibenzofuran-3-one. Yield: 57.5g, 90%. Colourless crystals M. pt. 140° – 143° C.

Step B—8,9bβ-dimethyl-1,2,3,4,4aβ,9b-hexahydro-4α-[3-(4-methylpiperazin-1-yl)-propionamido]-dibenzofuran-3-one dihydrochloride The 8,9bβ-dimethyl-1,2,3,4,4aβ,9b-hexahydro-4α-(3-chloropropionamido)-dibenzofuran-3-one (40g, 0.125 mole) and N-methyl piperazine (31g, 0.31 mole) were heated under reflux overnight in dry benzene (700 mls). T.L.C. then showed no starting material remaining and so the reaction mixture was poured onto water (500 mls) and the organic layer was separated. The organic layer was washed once more with water and was then dried over magnesium sulphate. The solvent was removed under reduced pressure giving a yellow oil. Low Rf material was removed using a silica wash from 5% methanol/chloroform and the dihydrochloride was prepared by adding excess methanolic hydrogen chloride to the oil in methanol. The 8,9bβ-dimethyl-1,2,3,4,4a,9b-hexahydro-4α-[3-(4-methylpiperazin-1-yl)-propionamido]-dibenzofuran-3-one dihydrochloride was collected and recrystallized from methanol, giving three crops, total 38.2g, 69% yield. M. pt. 215° – 218° C (capillary tube).

EXAMPLES 2 TO 25 a. The starting material of formula V was prepared as in Preparation 1 b. Using a similar method to that used in the preparation of 8,9bβ-dimethyl-1,2,3,4,4aβ,9b-hexahydro-4α-

(3-chloropropionamido)-dibenzofuran-3-one (as in stage A of Example 1), products of formula VII were prepared as in Table 1 below. The products were prepared by reacting the starting material of formula V obtained with the corresponding acyl halide of formula VI.

i. In examples 14 to 17 and 22 to 25 benzene was replaced by toluene.

ii. Azeotropic conditions were used in examples 7, 11, 13 to 15 and 17.

iii. The product of example 13 was purified by chromatography on alumina; the products of examples 21 and 23 to 25 were purified by chromatography on silica gel.

iv. Hydrochlorides of the products of formula I were prepared by treating monoamines with ethereal hydrogen chloride and diamines with methanolic hydrogen chloride.

Table 1

(VII) structure: dibenzofuran derivative with $H_3C$, $CH_3$, O, and $NH-CO-(CH_2)_n-Hal$ substituents

| Products | n | Hal | Formula | m.p. °C | I.R. Spectra |
|---|---|---|---|---|---|
| a | 1 | —Cl | $C_{16}H_{18}NO_3Cl$ | 151 – 153 | 1690, 1736, 3320 |
| b | 2 | —Cl | $C_{17}H_{20}NO_3Cl$ | 140 – 143 | 1650, 1735, 3260 |
| c | 3 | —Cl | $C_{18}H_{22}NO_3Cl$ | 118 – 119 | 1640, 1730, 3260 |
| d | 4 | —Cl | $C_{19}H_{24}NO_3Cl$ | 109 – 109.5 | 1634, 1737, 3255 |
| e | 5 | —Br | $C_{20}H_{26}NO_3Br$ | 81 – 83 | 1638, 1735, 3260 |

Analysis for Products a to e

| Products | M.Wt. | Calculated | | | | Found | | | |
|---|---|---|---|---|---|---|---|---|---|
| | | C% | H% | N% | Cl% | C% | H% | N% | Cl% |
| a | 307,8 | 62,44 | 5,89 | 4,55 | 11,52 | 62,48 | 6,00 | 4,43 | 11,73 |
| b | 321,8 | 63,45 | 6,26 | 4,35 | 11,02 | 63,51 | 6,31 | 4,43 | 11,08 |
| c | 335,8 | 64,38 | 6,60 | 4,17 | 10,56 | 64,10 | 6,37 | 4,09 | 10,43 |
| d | 349,9 | 65,23 | 6,91 | 4,00 | — | 63,96 | 7,18 | 3,96 | — |
| e | 408,3 | 58,83 | 6,42 | 3,43 | Br % 19,57 | 58,77 | 6,48 | 3,43 | Br % 19,58 | c. Following a method analogous to that of Stage B in Example 1, other products of formula 1 were prepared as shown in Table 2 below. The starting material of formula VII was reacted with the reagent of formula VIII in benzene and the product isolated as in Example 1 with the following exceptions:

Table 2

(I) structure: dibenzofuran derivative with $H_3C$, $CH_3$, O, and $NH-CO-(CH_2)_n-N(R_1)(R_2)$ substituents

| Ex. No. | n | —N(R_1)(R_2) | Salt | Empirical Formula | m.p. (°C) | I.R.Spectra (cm⁻¹) |
|---|---|---|---|---|---|---|
| 2 | 1 | dimethylamino | — | $C_{18}H_{24}N_2O_3$ | 108–110 | 1680, 1735, 3360 |
| 3 | 1 | morpholino | — | $C_{20}H_{26}N_2O_4$ | 125–128 | 1680, 1735, 3350 |
| 4 | 1 | 4-methylpiperzin-1-yl | 2 HCl | $C_{21}H_{31}N_3O_3Cl_2$ | 155–160 | 1700, 1741 |
| 5 | 1 | piperidino | HCl | $C_{21}H_{29}N_2O_3Cl$ | 112–115 | 1683, 1742 |
| 6 | 1 | diethylamino | HCl | $C_{20}H_{29}N_2O_3Cl$ | 108–111 | 1687, 1744 |
| 7 | 1 | pyrrolidine | — | $C_{20}H_{26}N_2O_3$ | 88–89 | 1680, 1735, 3380 |
| 8 | 1 | (N-ethyl)benzylamino- | HCl | $C_{25}H_{31}N_2O_3Cl$ | 110–114 | 1684, 1740 |
| 9 | 2 | morpholino | HCl | $C_{21}H_{29}N_2O_4Cl$ | 130–135 | 1650, 1742 |
| 10 | 2 | dimethylamine | HCl | $C_{19}H_{27}N_2O_3Cl$ | 115–120 | 1665, 1736 |
| 11 | 2 | pyrrolidino | HCl | $C_{21}H_{29}N_2O_3Cl$ | 120–124 | 1670, 1738 |
| 12 | 2 | piperidino | HCl | $C_{22}H_{31}N_2O_3Cl$ | 117–120 | 1673, 1738 |
| 13 | 2 | piperazino | 2 HCl | $C_{21}H_{31}N_3O_3Cl_2$ | 186–189 | 1665, 1735 |
| 14 | 2 | 4-ethoxycarbonyl-piperazin-1-yl | — | $C_{24}H_{33}N_3O_5$ | 189–190 | 1673, 1708, 1737 3230 |
| 15 | 2 | 4-phenylpiperazin-1-yl | 2 HCl | $C_{27}H_{35}N_3O_3Cl_2$ | 149–152 | 1678, 1736 |
| 16 | 2 | 4-(β-hydroxyethyl)-piperazin-1-yl | 2 HCl | $C_{23}H_{35}N_3O_4Cl_2$ | 130–145 | 1671, 1736 |
| 17 | 2 | 4-benzylpiperazin-1-yl | — | $C_{28}H_{35}N_3O_3$ | 207–211 | 1671, 1737 |
| 18 | 2 | N-methyl-2-(dimethylamino)-ethylamino | 2 HCl | $C_{23}H_{35}N_3O_3Cl_2$ | 135–142 | 1670, 1735 |
| 19 | 2 | diethylamino | HCl | $C_{21}H_{31}N_2O_3Cl$ | 57–62 | 1671, 1737 |

Table 2-continued (I) 7-methyl-dibenzofuran-hexahydro core with NH—CO—(CH$_2$)$_n$—NR$_1$R$_2$ substituent

| Ex. No. | n | —NR$_1$R$_2$ | Salt | Empirical Formula | m.p. (°C) | I.R.Spectra (cm$^{-1}$) |
|---|---|---|---|---|---|---|
| 20 | 2 | 4-acetylpiperazin-1-yl | HCl | C$_{23}$H$_{32}$N$_3$O$_4$Cl | 130–135 | 1660(Vb), 1742 |
| 21 | 2 | 4-ethylpiperazin-1-yl | 2 HCl | C$_{23}$H$_{35}$N$_3$O$_3$Cl$_2$ | 158–161 | 1670, 1735 |
| 22 | 3 | 4-methylpiperazin-1-yl | 2 HCl | C$_{23}$H$_{35}$N$_3$O$_3$Cl$_2$ | 192–196 | 1653, 1740 |
| 23 | 3 | dimethylamino | HCl | C$_{20}$H$_{29}$N$_2$O$_3$Cl | | 1673, 1737 |
| 24 | 4 | " | HCl | C$_{21}$H$_{31}$N$_2$O$_3$Cl | | 1671, 1739 |
| 25 | 5 | " | HCl | C$_{22}$H$_{33}$N$_2$O$_3$Cl | | 1671, 1740 |

Analysis of some of the compounds prepared in the Examples are given below

| Product of Example No. | M.Wt. | Calculated | | | | Found | | | |
|---|---|---|---|---|---|---|---|---|---|
| | | C% | H% | N% | Cl% | C% | H% | N% | Cl% |
| 1 | 458,4 | 55,46 | 7,40 | 8,82 | 14,88 | 55,22 | 7,29 | 8,71 | 14,96 |
| 3 | 358,4 | 67,02 | 7,31 | 7,82 | — | 67,12 | 7,56 | 7,58 | — |
| 4 | 444,4 | 54,54 | 7,19 | 9,09 | 15,33 | 54,31 | 7,10 | 8,74 | 15,54 |
| 7 | 342,4 | 70,15 | 7,65 | 8,18 | — | 70,45 | 7,74 | 8,18 | — |
| 9 | 508,9 | 58,58 | 7,35 | 6,50 | — | 58,68 | 7,51 | 6,29 | — |
| 10 | 366,9 | 62,20 | 7,42 | 7,63 | 9,66 | 62,04 | 7,66 | 7,38 | 9,69 |
| 11 | 392,9 | 58,80 | 7,75 | 6,53 | 8,26 | 58,83 | 7,72 | 6,72 | 8,53 |
| 12 | 406,9 | 63,53 | 7,75 | 6,73 | 8,52 | 63,62 | 7,90 | 6,73 | 8,81 |
| 13 | 444,4 | 54,34 | 7,19 | 9,09 | 15,33 | 54,62 | 7,33 | 8,99 | 15,52 |
| 14 | 443,5 | 64,99 | 7,50 | 9,47 | — | 65,13 | 7,72 | 9,24 | — |
| 17 | 461,6 | 72,86 | 7,64 | 9,10 | — | 72,89 | 7,51 | 9,04 | — |
| 20 | 450,0 | 61,39 | 7,17 | 9,34 | 7,88 | 61,24 | 7,38 | 9,09 | 7,98 |
| 22 | 472,5 | 56,32 | 7,60 | 8,57 | 14,46 | 56,26 | 7,44 | 8,55 | 14,51 |

EXAMPLE 26—SYRUP

A syrup was prepared with the following formulation: 8,9bβ-dimethyl-1,2,3,4,4aβ,9b-hexahydro-4α[3-(4-methylpiperazin-1-yl)-propionamido]-dibenzo-furan-3-one dihydrochloride. . . 0.3 g Flavoured and sweetened excipient. . . q.s.p. 100 ml.

EXAMPLE 27—TABLETS

Tablets were prepared with the following formulation: 8,9bβ-dimethyl-1,2,3,4,4aβ,9b-hexahydro-4α[3-(4-methylpiperazin-1-yl)-propionamido]-dibenzo-furan-3-one hydrochloride. . . 25 g Excipient. . . q.s.p. for one tablet. (Excipient: lactose, starch, talc, magnesium stearate).

PHARMACOLOGICAL ACTIVITY

1. Antitussive activity

The antitussive effect of the compounds was studied on a cough experimentally induced by electric stimulation of the vagus nerve in the guinea pig.

The test consists of stimulating the vagus nerve of the guinea pig and repeating the stimulus 20 and 40 minutes after oral administration of 100 mg/kg of the product under test. 6 Negative responses (3 after 20 minutes and 3 after 40 minutes) represent a cough inhibition of 100%. The test was carried out in groups of 6 animals against groups of control animals (undosed).

The results obtained, expressed as percentage inhibition are shown in Table 3 below.

In addition, for certain compounds the ED$_{50}$ was also determined, i.e. that dose which reduces the number of coughs by 50%. For the products of Examples 1 and 24 the ED$_{50}$ was found to be 32.5 mg/kg and 71 mg/kg respectively.

Table 3

![structure]

| Ex. No. | n | —N(R₁)(R₂) | Salt | Percentage cough inhibition |
|---|---|---|---|---|
| 1 | 2 | 4-methylpiperazin-1-yl | 2 HCl | 100 |
| 4 | 1 | 4-methylpiperazin-1-yl | 2 HCl | 43 |
| 7 | 1 | pyrrolidino | — | 17 |
| 9 | 2 | morpholino | HCl | 39 |
| 10 | 2 | dimethylamino | HCl | 89 |
| 11 | 2 | pyrrolidino | HCl | 44 |
| 12 | 2 | piperidino | HCl | 46 |
| 13 | 2 | piperazino | 2 HCl | 75 |
| 14 | 2 | 4-ethoxycarbonylpiperazin-1-yl | — | 33 |
| 15 | 2 | 4-phenylpiperazin-1-yl | 2 HCl | 54 |
| 16 | 2 | 4-(β-hydroxymethyl)-piperazin-1-yl | 2 HCl | 17 |
| 17 | 2 | 4-benzylpiperazin-1-yl | — | 33 |
| 18 | 2 | N-methyl-2-(dimethylamino)-ethylamino | 2 HCl | 50 |
| 19 | 2 | diethylamino | HCl | 33 |
| 20 | 2 | 4-acetylpiperazin-1-yl | HCl | 33 |
| 22 | 3 | 4-methylpiperazin-1-yl | 2 HCl | 72 |
| 23 | 3 | dimethylamino | HCl | 67 |
| 24 | 4 | " | HCl | 83 |
| 25 | 5 | " | HCl | 25 |

The results obtained show that the compounds of the present invention possess important antitussive activity, particularly the products of Examples 1, 10 and 24.

2. Acute Toxicity

The acute toxicity of some of compounds of the invention was determined on guinea pigs which had received an increasing oral dose of the compound.
The results are shown in Table 4.

Table 4

| Compound of Example No. | LD₅₀ in mg/kg |
|---|---|
| 1 | 1475 |
| 4 | > 800 |
| 7 | ~ 800 |
| 8 | > 800 |
| 10 | 500–1000 |
| 11 | ~ 600 |
| 12 | ~ 400 |
| 13 | > 1000 |
| 14 | > 1000 |
| 17 | > 1000 |
| 18 | > 1000 |
| 20 | > 1000 |
| 21 | > 1000 |

These demonstrate the low toxicity of the compounds of the invention.

What we claim is:
1. A compound of the formula:

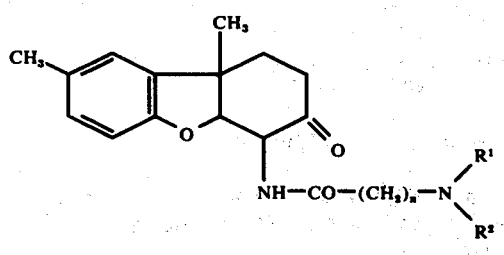

wherein $R^1$ and $R^2$, which may be the same or different, represent methyl, ethyl, benzyl or dimethylaminoethyl groups or together with the intervening N represents a pyrrolidino, piperidino, morpholino, piperazino, or piperazino having in the 4-position a methyl, ethyl, hydroxyethyl, phenyl, benzyl, acetyl or ethoxycarbonyl group, n is an integer less than 6, and a pharmaceutically acceptable salt thereof.

2. A compound as claimed in claim 1 wherein $R^1$ and $R^2$ are methyl or together form a 4-methyl piperazino group.

3. A compound of claim 1 which is 8,9bβ-dimethyl-1,2,3,4,4aβ,9b-hexahydro-4α[3-(4-methylpiperazino)-propionamido]-dibenzofuran-3-one; 8,9bβ-dimethyl-1,2,3,4,4aβ,9b-hexahydro-4α[3-N,N-dimethylamino-propionamido]dibenzofuran-3-one; 8,9bβ-dimethyl-1,2,3,4,4aβ,9b-hexahydro-4α[3-piperazino-propionamido]-dibenzofuran-3-one; 8,9bβ-dimethyl-1,2,3,4,4aβ,9b-hexahydro-4α[4-(4-methyl piperazino)butyramido] dibenzofuran-3-one; or 8,9bβ-dimethyl-1,2,3,4,4aβ,9b-hexahydro-4α-[5-N,N-dimethylaminovaleramido]dibenzofuran-3-one.

4. A compound of claim 3 which is a pharmaceutically acceptable acid addition salt thereof.

5. A pharmaceutically acceptable acid addition salt of claim 4 which is formed with hydrochloric, hydrobromic, nitric, sulphuric, phosphonic, acetic, formic, benzoic, maleic, fumaric, succinic, tartaric, citric, oxalic, benzilic, glyoxylic, aspartic, methanesulphonic or p-toluenesulphonic acid.

6. A pharmaceutical composition consisting essentially of a compound of claim 1 together with a pharmaceutical carrier or excipient.

7. A pharmaceutical composition as claimed in claim 6 in dosage units containing 5–50 mg/unit.

8. A pharmaceutical composition as claimed in claim 6 in the form of tablets, syrups, capsules, granules, solutions and linctuses.

9. A method of controlling various forms of cough consisting essentially of administering a cough controlling amount of a compound of claim 1.

* * * * *